(12) United States Patent
Buysse et al.

(10) Patent No.: US 9,763,728 B2
(45) Date of Patent: Sep. 19, 2017

(54) ABLATION NEEDLE GUIDE

(71) Applicant: COVIDIEN LP, Mansfield, MA (US)

(72) Inventors: Steven P. Buysse, Niwot, CO (US); Casey M. Ladtkow, Erie, CO (US); Joshua K. Buysse, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/056,160

(22) Filed: Feb. 29, 2016

(65) Prior Publication Data

US 2016/0206364 A1 Jul. 21, 2016

Related U.S. Application Data

(62) Division of application No. 12/135,690, filed on Jun. 9, 2008, now Pat. No. 9,271,796.

(51) Int. Cl.
*A61B 18/12* (2006.01)
*A61B 18/14* (2006.01)
*A61B 90/11* (2016.01)
*A61B 18/00* (2006.01)

(52) U.S. Cl.
CPC .......... *A61B 18/14* (2013.01); *A61B 18/1206* (2013.01); *A61B 90/11* (2016.02); *A61B 18/1477* (2013.01); *A61B 2018/0016* (2013.01); *A61B 2018/00023* (2013.01); *A61B 2018/00577* (2013.01); *A61B 2018/143* (2013.01); *A61B 2018/1405* (2013.01); *A61B 2018/1425* (2013.01); *A61B 2018/1495* (2013.01)

(58) Field of Classification Search
CPC ..... A61B 18/14; A61B 18/1477; A61B 18/16; A61B 2018/143; A61B 2018/1405; A61B 2018/1425; A61B 2018/1495; A61B 2018/165; A61B 2018/167; A61B 2018/0016; A61B 90/11
USPC ...... 606/35, 41, 44, 47, 129, 34; 607/98, 99, 607/116
See application file for complete search history.

(56) References Cited

U.S. PATENT DOCUMENTS

| | | |
|---|---|---|
| 3,631,363 A | 12/1971 | Miller |
| D263,020 S | 2/1982 | Rau, III |
| 4,397,313 A | 8/1983 | Vaguine |
| 4,462,412 A | 7/1984 | Turner |
| 4,572,190 A | 2/1986 | Azam et al. |

(Continued)

FOREIGN PATENT DOCUMENTS

| | | |
|---|---|---|
| DE | 390937 C | 3/1924 |
| DE | 1099658 B | 2/1961 |

(Continued)

OTHER PUBLICATIONS

U.S. Appl. No. 08/483,742, filed Jun. 7, 1995.

(Continued)

*Primary Examiner* — Thomas Giuliani

(57) ABSTRACT

A guide block introduces electrodes into target tissue and includes an elongated, generally rectilinear bar having a plurality of slots defined therethrough. Each of the slots is configured to selectively receive and retain a corresponding electrode therein. The rectilinear bar is malleable and selectively bendable from a substantially linear configuration to a substantially curved configuration to facilitate positioning the guide block relative to target tissue.

8 Claims, 11 Drawing Sheets

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| 4,798,215 A | 1/1989 | Turner | |
| 5,097,844 A | 3/1992 | Turner | |
| 5,417,210 A | 5/1995 | Funda et al. | |
| 5,449,360 A | 9/1995 | Schreiber | |
| 5,626,607 A | 5/1997 | Malecki et al. | |
| 6,031,375 A | 2/2000 | Atalar et al. | |
| D424,694 S | 5/2000 | Tetzlaff et al. | |
| D425,201 S | 5/2000 | Tetzlaff et al. | |
| 6,241,725 B1 | 6/2001 | Cosman | |
| 6,267,770 B1 | 7/2001 | Truwit | |
| D449,886 S | 10/2001 | Tetzlaff et al. | |
| 6,355,033 B1 | 3/2002 | Moorman et al. | |
| 6,375,606 B1 | 4/2002 | Garibaldi et al. | |
| D457,958 S | 5/2002 | Dycus et al. | |
| D457,959 S | 5/2002 | Tetzlaff et al. | |
| 6,564,806 B1 | 5/2003 | Fogarty et al. | |
| 6,585,733 B2 * | 7/2003 | Wellman | A61B 18/1477 606/41 |
| 6,603,994 B2 | 8/2003 | Wallace et al. | |
| 6,652,520 B2 | 11/2003 | Moorman et al. | |
| 6,725,080 B2 | 4/2004 | Melkent et al. | |
| D496,997 S | 10/2004 | Dycus et al. | |
| 6,807,446 B2 | 10/2004 | Fenn et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,197,363 B2 | 3/2007 | Prakash et al. | |
| D541,418 S | 4/2007 | Schechter et al. | |
| D541,938 S | 5/2007 | Kerr et al | |
| 7,223,264 B2 | 5/2007 | Daniel et al. | |
| 7,226,446 B1 | 6/2007 | Mody et al. | |
| 7,278,991 B2 | 10/2007 | Morris et al. | |
| 7,282,049 B2 | 10/2007 | Orszulak et al. | |
| D564,662 S | 3/2008 | Moses et al. | |
| 7,422,586 B2 | 9/2008 | Morris et al. | |
| 7,439,736 B2 | 10/2008 | Meaney et al. | |
| 7,467,015 B2 | 12/2008 | van der Weide | |
| 7,565,207 B2 | 7/2009 | Turner et al. | |
| 9,271,796 B2 | 3/2016 | Buysse et al. | |
| 2002/0022836 A1 | 2/2002 | Goble et al. | |
| 2002/0111615 A1 * | 8/2002 | Cosman | A61B 18/1477 606/41 |
| 2002/0120261 A1 * | 8/2002 | Morris | A61B 18/1477 606/41 |
| 2004/0039429 A1 | 2/2004 | Daniel et al. | |
| 2004/0097805 A1 | 5/2004 | Verard et al. | |
| 2004/0242992 A1 | 12/2004 | Hareyama | |
| 2004/0267256 A1 * | 12/2004 | Garabedian | A61B 18/1482 606/41 |
| 2005/0137662 A1 | 6/2005 | Morris et al. | |
| 2006/0079887 A1 | 4/2006 | Buysse et al. | |
| 2006/0122581 A1 | 6/2006 | Ein-Gal | |
| 2006/0142757 A1 | 6/2006 | Daniel et al. | |
| 2007/0203480 A1 | 8/2007 | Mody et al. | |
| 2008/0009852 A1 | 1/2008 | Fernald et al. | |
| 2008/0021448 A1 | 1/2008 | Orszulak et al. | |
| 2009/0171203 A1 | 7/2009 | Avital et al. | |

FOREIGN PATENT DOCUMENTS

| | | | |
|---|---|---|---|
| DE | 1139927 B | 11/1962 | |
| DE | 1149832 B | 6/1963 | |
| DE | 1439302 A1 | 1/1969 | |
| DE | 2439587 A1 | 2/1975 | |
| DE | 2455174 A1 | 5/1975 | |
| DE | 2407559 A1 | 8/1975 | |
| DE | 2415263 A1 | 10/1975 | |
| DE | 2429021 A1 | 1/1976 | |
| DE | 2460481 A1 | 6/1976 | |
| DE | 2602517 A1 | 7/1976 | |
| DE | 2504280 A1 | 8/1976 | |
| DE | 2627679 A1 | 1/1977 | |
| DE | 2540968 A1 | 3/1977 | |
| DE | 2820908 A1 | 11/1978 | |
| DE | 2803275 A1 | 8/1979 | |
| DE | 2823291 A1 | 11/1979 | |
| DE | 2946728 A1 | 5/1981 | |
| DE | 3143421 A1 | 5/1982 | |
| DE | 3045996 A1 | 7/1982 | |
| DE | 3120102 A1 | 12/1982 | |
| DE | 3510586 A1 | 10/1986 | |
| DE | 3604823 A1 | 8/1987 | |
| DE | 8712328 U1 | 2/1988 | |
| DE | 3711511 C1 | 6/1988 | |
| DE | 3904558 A1 | 8/1990 | |
| DE | 3942998 A1 | 7/1991 | |
| DE | 4238263 A1 | 5/1993 | |
| DE | 04303882 C2 | 2/1995 | |
| DE | 4339049 A1 | 5/1995 | |
| DE | 29616210 U1 | 11/1996 | |
| DE | 19608716 C1 | 4/1997 | |
| DE | 19751106 A1 | 5/1998 | |
| DE | 19717411 A1 | 11/1998 | |
| DE | 19751108 A1 | 5/1999 | |
| DE | 19801173 C1 | 7/1999 | |
| DE | 19848540 A1 | 5/2000 | |
| DE | 10224154 A1 | 12/2003 | |
| DE | 10328514 B3 | 3/2005 | |
| DE | 102004022206 A1 | 12/2005 | |
| DE | 202005015147 U1 | 2/2006 | |
| EP | 0 246 350 A1 | 11/1987 | |
| EP | 0 481 685 A1 | 4/1992 | |
| EP | 0 521 264 A2 | 1/1993 | |
| EP | 0541930 A1 | 5/1993 | |
| EP | 0 556 705 A1 | 8/1993 | |
| EP | 0 558 429 A1 | 9/1993 | |
| EP | 0572131 A1 | 12/1993 | |
| EP | 0 836 868 A2 | 4/1998 | |
| EP | 0 882 955 A1 | 12/1998 | |
| EP | 1 070 518 A2 | 1/2001 | |
| EP | 1186274 A2 | 3/2002 | |
| EP | 1278007 A1 | 1/2003 | |
| EP | 1159926 A3 | 3/2003 | |
| EP | 1 645 234 A1 | 4/2006 | |
| EP | 1645235 A1 | 4/2006 | |
| EP | 1 810 627 A1 | 7/2007 | |
| FR | 179 607 | 11/1906 | |
| FR | 1 275 415 A | 11/1961 | |
| FR | 1 347 865 A | 1/1964 | |
| FR | 2 235 669 A1 | 1/1975 | |
| FR | 2 276 027 A1 | 1/1976 | |
| FR | 2 313 708 A1 | 12/1976 | |
| FR | 2 502 935 A1 | 10/1982 | |
| FR | 2 517 953 A1 | 6/1983 | |
| FR | 2 573 301 A1 | 5/1986 | |
| FR | 2 862 813 A1 | 5/2005 | |
| FR | 2 864 439 A1 | 7/2005 | |
| JP | 5-5106 | 1/1993 | |
| JP | 05-40112 | 2/1993 | |
| JP | 06343644 A | 12/1994 | |
| JP | 07265328 A | 10/1995 | |
| JP | 08056955 | 3/1996 | |
| JP | 08252263 A | 10/1996 | |
| JP | 09010223 | 1/1997 | |
| JP | 11244298 A | 9/1999 | |
| JP | 2000342599 A | 12/2000 | |
| JP | 2000350732 A | 12/2000 | |
| JP | 2001008944 A | 1/2001 | |
| JP | 2001029356 A | 2/2001 | |
| JP | 2001128990 A | 5/2001 | |
| JP | 2008142467 A | 6/2008 | |
| SU | 166452 | 1/1965 | |
| SU | 401367 A1 | 10/1973 | |
| SU | 727201 A2 | 4/1980 | |
| WO | 97/41924 A1 | 11/1997 | |
| WO | 97/43971 A2 | 11/1997 | |
| WO | 9904710 A1 | 2/1999 | |
| WO | 00/48672 A1 | 8/2000 | |
| WO | 00/51513 A1 | 9/2000 | |

(56) References Cited

FOREIGN PATENT DOCUMENTS

| WO | 01/01847 A1 | 1/2001 |
|---|---|---|
| WO | 01/74252 A2 | 10/2001 |
| WO | 02/45790 A2 | 6/2002 |
| WO | 02/061880 A2 | 8/2002 |
| WO | 2004/112628 A1 | 12/2004 |
| WO | 2005/016119 A2 | 2/2005 |
| WO | 2005009528 A1 | 2/2005 |

OTHER PUBLICATIONS

U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T.Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "Ligasure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.

(56) References Cited

OTHER PUBLICATIONS

European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European. Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndotHill, vol. III, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part 1", (2001) J Vasc. Interv. Radiol, vol. 12, pp. 1021-1032.

(56) References Cited

OTHER PUBLICATIONS

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure.TM. Vessel Sealing System: A Case Report" Innovations That Work, Feb. 2002.

Humphries Jr. et al., "Finite.cndot.Element Codes to Model Electrical Heating and Non-Linear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure.TM. Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure.TM. Vessel Sealing System in Hemorrhoidectormy" American College of Surgeons (ACS) Clinic La Congress Poster (2000).

Johnson, "Use of the LigaSure.TM. Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure.TM. System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure.TM. Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure. TM. Vessel Sealing System and LigaSure.TM. Atlas 20 cm Open Instrument" Innovations That Work, Jun. 2003.

Muller et al., "Extended Left Hemicolectomy Using the LigaSure. TM. Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,767, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(56) References Cited

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/ Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.

\* cited by examiner

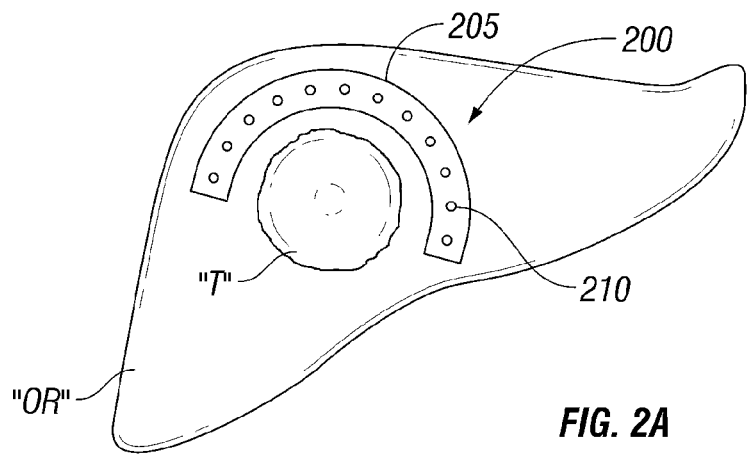
FIG. 2A
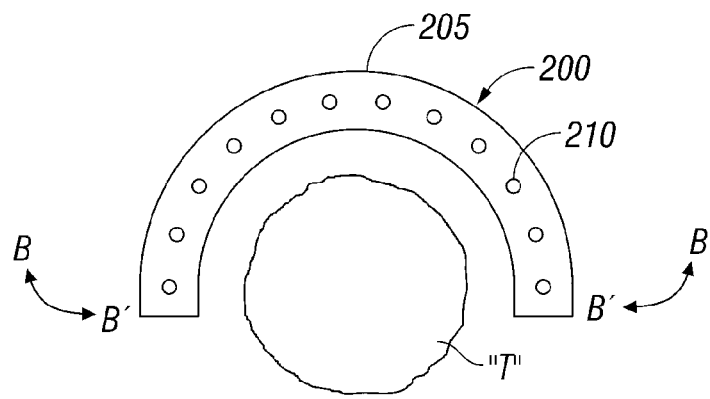
FIG. 2B
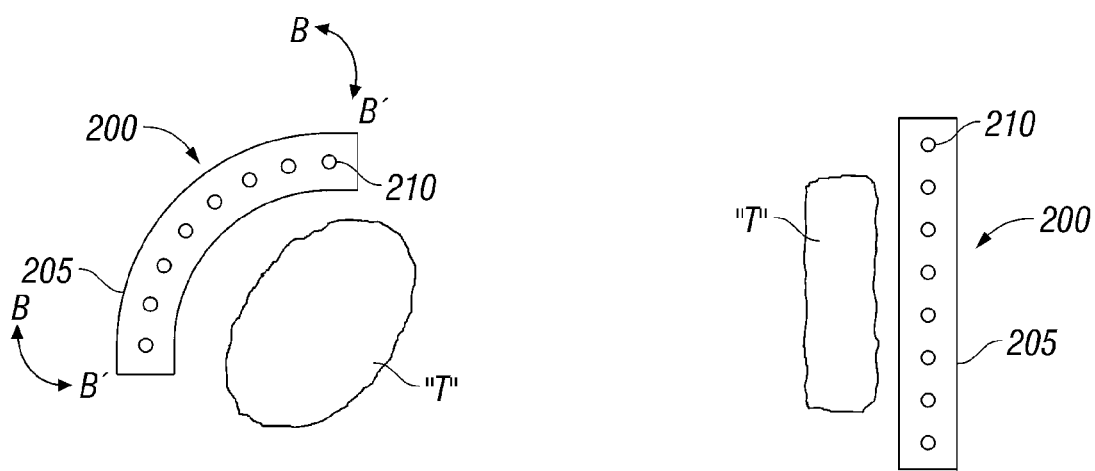
FIG. 2C
FIG. 2D

ABLATION NEEDLE GUIDE

CROSS-REFERENCE TO RELATED APPLICATIONS

This application is a divisional application of U.S. patent application Ser. No. 12/135,690, filed on Jun. 9, 2008 (now U.S. Pat. No. 9,271,796), the entire contents of which are incorporated by reference herein.

BACKGROUND

Technical Field

The present disclosure relates generally to ablation electrode systems and, more particularly, to systems, devices and methods for positioning and placing multiple electrodes in a target surgical site.

Background of Related Art

The use of radiofrequency electrodes for ablation of tissue in a patient's body is known. In a typical situation, a radiofrequency electrode comprising an elongated, cylindrical shaft with a portion of its external surface insulated is inserted into the patient's body. The electrode typically has an exposed conductive tip, which is used to contact body tissue in the region where the heat lesion or ablation is desired. The electrode is connected to a radiofrequency power source, which provides radiofrequency voltage to the electrode, which transmits the radiofrequency current into the tissue near its exposed conductive tip. This current usually returns to the power source through a concentric electrode in a bipolar system or through a reference electrode in a monopolar system. The reference electrode may comprise a large area conductive contact or pad connected to an external portion of the patient's body.

In some applications, e.g., wedge resections (segmentectomies) or tumor ablation procedures, multiple electrodes are inserted into the body in an array or partial array to enlarge ablation volumes and specifically define resection areas. For example, in some particular applications, arrays of high frequency electrodes are inserted into tumors and energized to create an ablation volume depending upon the particular positioning of the electrodes. The electrodes are typically placed in a dispersed fashion throughout the tumor volume to cover the tumor volume with uniform heat, typically above about 45° C. The electrodes may be sequentially applied with high frequency voltage so that each electrode heats in sequence its neighboring tissue and then shuts off. Then, the next electrode does the same in a time series. This sequence of cycling the voltage through the electrodes continues at a prescribed frequency and for a period of time until the tumor is ablated.

Desirably, a configuration of radiofrequency electrodes, which can accomplish ablation in the range of 4 to 6 cm diameter or greater for the purpose of adequately treating large cancerous tumors in the body are necessary to effectively destroy the tumor and combat cancerous cells from spreading. It is further necessary that such an electrode system involve a simple geometry, reduced numbers of tissue insertions, facilitate planning of needle placement, and facilitate planning of heat ablation geometry and distribution. Typically, an introducer is provided for this purpose and to facilitate the insertion of a "cluster" of electrodes into the body for performing tissue ablation. The introducer includes a body portion including one or more holes formed therein for selectively receiving a respective elongate shaft of the electrodes therethrough. The holes of the introducer orient and space each electrode relative to one another according to the geometry of the introducer.

SUMMARY

The present disclosure relates to systems, devices and methods for positioning and placing multiple electrodes in a target surgical site.

According to one aspect of the present disclosure an electrode system is provided for use with a high frequency generator to induce coherent high frequency heat ablation volumes within targeted tissue of a patient. The electrode system includes a hub; and a plurality of electrodes. Each electrode includes a substantially rigid elongated shaft extending from the hub and terminating in a sealed distal end section having an exposed conductive tip portion configured to be inserted into the targeted tissue and adapted at a proximal end section to be coupled to a high frequency generator to simultaneously apply an equal output voltage to each of the exposed conductive tip portions. Each electrode further includes a closed-loop fluid communication channel pathway which includes an inflow opening adapted for connection to a coolant fluid supply, and a channel portion in fluid communication with the inflow opening. The channel portion extends distally inside the conductive tip portion to carry coolant to the inside of the conductive tip portion and further extends proximally back to an outlet opening adapted to carry coolant away from the conductive tip portion.

The electrode system further includes a guide block for introducing electrodes into target tissue having an elongated, generally rectilinear bar including a plurality of slots defined therethrough. Each of the slots is configured to selectively receive and retain a corresponding electrode therein. The rectilinear bar is malleable and selectively bendable from a substantially linear configuration to a substantially curved configuration to facilitate positioning the guide block relative to target tissue. One or more of the plurality of slots is disposed through the bar at an angle relative to the top and bottom surfaces of the rectilinear bar. Different slots may be disposed at different angles.

In one embodiment, the corresponding plurality of electrodes are simultaneously and/or sequentially activated to create an ablation plane or ablation plume. In another embodiment, one or more electrodes is selectively repositionable within the plurality of slots and simultaneously and/or sequentially activated to create an ablation plane or plume.

The present disclosure also relates to a guide block for introducing electrodes into target tissue including an elongated, generally rectilinear bar having a plurality of individual segments arranged in a nested series along a longitudinal axis defined therethrough. Each of the segments includes one or more slots defined therethrough configured to selectively receive and retain a corresponding electrode therein. Each segment includes one or more facets angled relative to a line normal to the longitudinal axis to allow each of the segments to rotate relative to an adjacent segment in the nested series and relative to the longitudinal axis. The communitive effect of each of the segments in the nested series rotating about the longitudinal axis allows the guide block to bend to at least a substantially circular configuration.

In one embodiment, each segment includes one or more slots disposed therethrough and a first interface and a second interface. The first interface is configured to matingly engage a distally adjacent segment of the plurality of segments and the second interface is configured to matingly engage a proximally adjacent segment of the plurality of segments. In another embodiment, each segment includes two opposing side facets disposed at a first angle and two opposing top and bottom facets disposed at a second angle. The side facets allows rotation of the guide block in a transverse direction relative to the longitudinal axis and the top and bottom facets allow rotation of the guide block in a vertical direction relative to the longitudinal axis. One or more of the segments may include one or more slots disposed at various angles relative to the top and bottom surfaces through the segment.

In yet another embodiment a locking clip is included which selectively secures two adjacent segments of the plurality of segments in the nested configuration. In still another embodiment, at least two adjacent segments of the plurality of segments are secured in a friction-fit manner.

The present disclosure also relates to a guide block for introducing electrodes into tissue including an elongated, generally rectilinear bar having a plurality of slots defined therethrough. Each of the slots is configured to selectively receive and retain a corresponding electrode therein. At least a portion of the guide block is adapted to connect to an electrosurgical generator such that the portion of the guide block (e.g., the bottom surface of the guide block) returns electrical energy back to the generator. Each of the plurality of slots may include a dielectric material disposed along an inner periphery thereof and the bar may be malleable to facilitate positioning the guide block relative to target tissue.

In one embodiment, a reference element is disposed on the guide block (or on one or more of the plurality of individual segments) that is configured to orient the guide block relative to an imaging source such as an ultrasonic scanning head.

BRIEF DESCRIPTION OF THE DRAWINGS

Various preferred embodiments of the presently disclosed systems, devices and methods are disclosed herein with reference to the drawings wherein:

FIG. 2A is a schematic illustration of the ablation needle guide positioned atop a patient's organ for guiding heated ablation needles to a targeted tissue area according to one embodiment of the present disclosure;

FIGS. 2B-2D are schematic views of a bendable ablation guide for use with various target tissue types;

DETAILED DESCRIPTION

Figure 1:
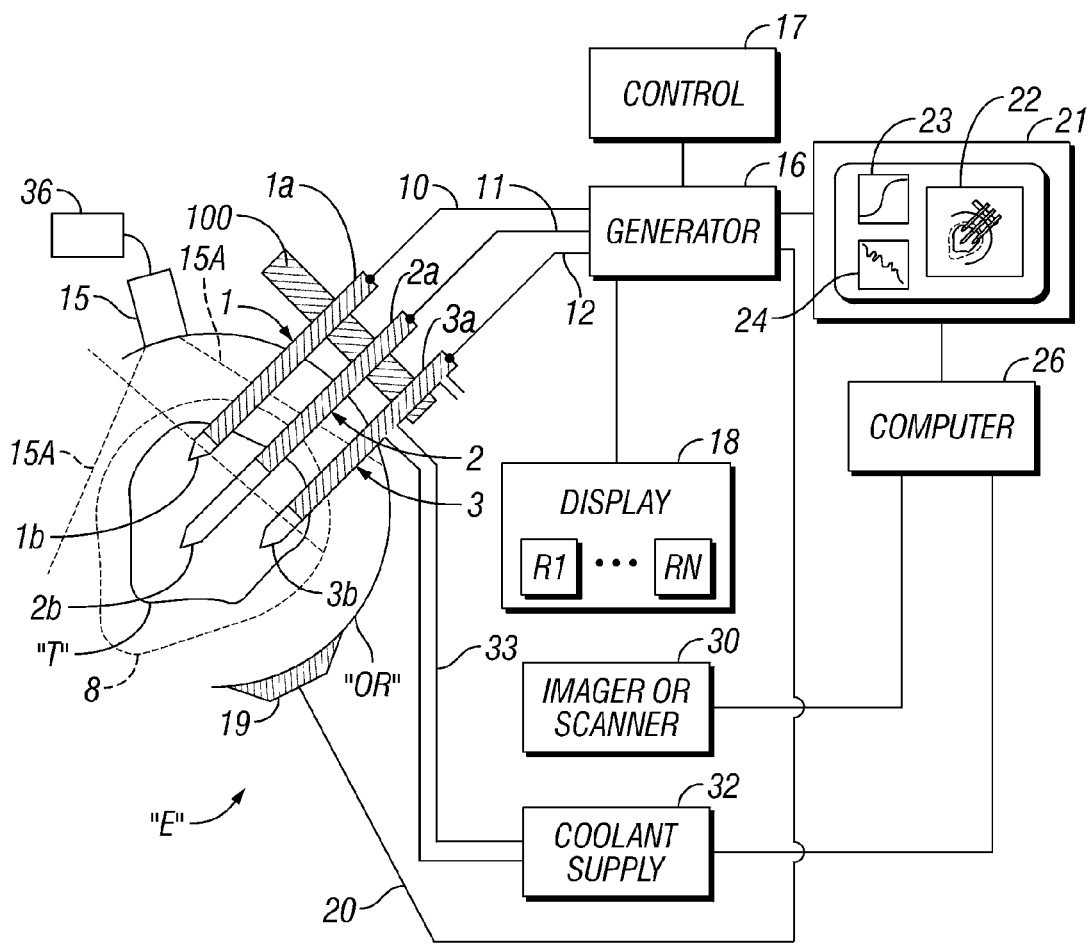
FIG. 1 is a schematic representation of an electrosurgical system for use with an ablation needle guide according to the present invention.

Referring initially to FIG. 1, an ablation electrode array system, in accordance with the present disclosure, is generally designated "E". Electrode array system "E" includes a plurality of electrodes 1, 2 and 3, which are configured for insertion into an organ "OR" of a human body or any other body tissue. Respective distal tips 1b, 2b and 3b of electrodes 1, 2 and 3 are typically un-insulated and conductively exposed so that electrical currents induce heating within the tissue or organ "OR". A targeted volume of tissue "T" is shown in sectional view and may represent, for example, a tumor or other abnormality in a human body.

Electrodes 1, 2 and 3 are connected by respective wires or cables 10, 11 and 12 to an electrosurgical generator 16. Electrosurgical generator 16 may be a radiofrequency or high frequency type generator. Electrosurgical generator 16 includes control elements, illustrated by block 17, which may, for example, increase the radiofrequency power output of electrodes 1, 2 and 3, control temperature when electrode array system "E" or satellite sensors (not shown) include temperature sensors, monitor or control impedance, power, current, voltage, or other output parameters. Electrosurgical generator 16 may include a display or screen, illustrated by block 18, within it or as a separate system, for providing a display of heating parameters such as temperature for one or more of electrodes 1, 2 and 3, impedance, power, current, or voltage of the radiofrequency output. Such individual display readings are illustrated by the reference letters R1 . . . RN.

Electrode system "E" further includes a reference electrode 19, which may be placed in contact with the skin of a patient or an external surface of organ "OR" with a connection 20 to electrosurgical generator 16. Reference electrode 19 and connection 20 serves as a path for return current from electrosurgical generator 16 through electrodes 1, 2 and 3.

Each electrode 1, 2 and 3 includes a rigid shaft 1a, 2a and 3a, respectively, which enables electrodes 1, 2 and 3 to be easily urged into the body tissue or organ "OR". Each electrode 1, 2 and 3 terminates pointed distal tips 1b, 2b and 3b, respectively. A portion of the external surface of each electrode 1, 2 and 3 may be covered with an insulating material, as indicated by hatched line areas in FIG. 1. Distal tips 1b, 2b and 3b are connected, through respective shafts 1a, 2a and 3a to cables 10, 11 and 12, respectively, and thereby to electrosurgical generator 16.

By way of example only and in no way to be considered as limiting, electrosurgical generator 16 may be a radiofrequency generator with frequency between about 100 kilohertz (kHz) to several hundred megahertz (MHz). Additionally, electrosurgical generator 16 may have power output ranging from several watts to several hundred watts, depending on the clinical application.

Electrodes 1, 2 and 3 may be raised to the same radiofrequency voltage potential from electrosurgical generator 16. The array of electrodes thus becomes, in effect, a larger, coherent electrode including the individual electrode tips 1b, 2b and 3b. Thus, the heating effect of the array of electrodes is substantially similar to that achieved by one large single electrode.

As seen in FIG. 1, by way of illustration only, a targeted region to be ablated is represented in sectional view by the line "T". It is desired to ablate the targeted region "T" by fully engulfing targeted region "T" in a volume of lethal heat elevation. The targeted region "T" may be, for example, a tumor which has been detected by an image scanner 30. For example, CT, MRI, or ultrasonic image scanners may be used, and the image data transferred to a computer 26. As an alternate example, an ultrasonic scanner head 15 may be disposed in contact with organ "OR" to provide an image illustrated by lines 15A. A data processor 36 may be connected to the display devices to visualize targeted region "T" and/or ablation zone in real time during the ablation procedure. A coolant supply 32 may also be integrated into the system via supply 33 to actively cool the electrodes 1, 2 and 3 as needed during the ablation.

An image 21 or graphical illustrations 23 and 24 of the scan may be displayed on display unit 21 to represent the size and position of target region "T". Placement of electrodes 1, 2 and 3 and relevant activation thereof may be predetermined based on such image data as interactively determined by real-time scanning of organ "OR". Electrodes 1, 2 and 3 may be inserted into the tissue by freehand technique, by stereotactic frame or frameless guidance or by a needle guide block or introducer 100 with multi-hole templates. The needle guide block 100 includes a reference surface (or reference feature 311—See FIG. 3A) that is oriented in a specific fashion to create a reference surface image such that the ultrasonic scanner head 15 can mate therewith (or be easily oriented with respect thereto) to facilitate placement of the electrodes 1, 2 and 3. In other words, the reference feature (e.g., element 311) interacts with the ultrasonic scanner head 15 and provides a point of reference to the guide block 100 to facilitate positioning of the electrodes 1, 2, and 3. This is particularly useful due to the guide block 100 being selectively bendable or positionable as explained in detailed herein. The electrodes 1, 2 and 3 may be simultaneously or sequentially activated to create an ablation plume. Simultaneous activation would be substantially similar to that achieved by one large single electrode. Alternatively, a single electrode, e.g., electrode 1, may be selectively positioned within a plurality of slots 210 (See FIG. 2A) disposed through the introducer or guide block 100.

An array of electrodes 1, 2 and 3 are connected to the same radiofrequency voltage from electrosurgical generator 16. Accordingly, the array of electrodes 1, 2 and 3 will act as a single, effectively larger electrode. The relative position, orientation and activation sequence or sequencing of electrodes 1, 2 and 3 enable the creation of different shapes and sizes of ablation volumes. For example, in FIG. 1, dashed line 8 represents the ablation isotherm in a sectional view through organ "OR". Such an ablation isotherm may be that of the surface achieving possible temperatures of approximately 50° C. or greater. At that temperature range, sustained for approximately 30 seconds to approximately several minutes, tissue cells will experience thermal damage. The shape and size of the ablation volume, as illustrated by dashed line 8, may accordingly be controlled by the configuration of the electrode array, electrode sequencing, the geometry of the distal tips 1b, 2b and 3b of electrodes 1, 2 and 3, respectively, the amount of RF power applied, the time duration that the power is applied, cooling of the electrodes, etc.

Turning now to FIGS. 2A-16, various embodiments of the needle guide block 100 are shown for use with the present electrosurgical system of FIG. 1. All of the envisioned needle guide blocks illustrated in FIGS. 2A-16 are designed for use with an electrode system "E" (or similar system, e.g., an antenna system) as described above. Each embodiment of the needle guide block is described in detail below with reference to the various figures and is described to the extent necessary to denote the particular point of novelty of the envisioned embodiment and will only be described in reference to the system "E" as is necessary to accomplish this purpose.

FIGS. 2A-2D show one embodiment of a needle guide block 200 which is selectively bendable or formable around a tumor "T". More particularly, the guide block 200 includes an elongated, generally rectangular bar 205 that is selectively malleable or bendable to optimally position electrodes 1, 2 and/or 3 around a target site. The bar 205 includes a plurality of slots or holes 210 defined therethrough which are each configured and dimensioned to selectively receive and retain an electrode 1, 2 and/or 3. As best shown in the comparison of FIGS. 2B-2C, the bar 205 is malleable or bendable in the direction of arrows "B" or "B'" from a substantially 90° configuration for partially encircling target tissue "T" (see FIG. 2B) to a partially arcuate configuration (See FIG. 2C) to a substantially straight configuration for treating more elongated target tissue areas "T" (See FIG. 2D). The user may selectively bend the bar 205 in any conceivable configuration to position the electrodes 1, 2 and/or 3 to treat target tissue "T" of having a variety of different shapes and volumes.

Figure 3A:
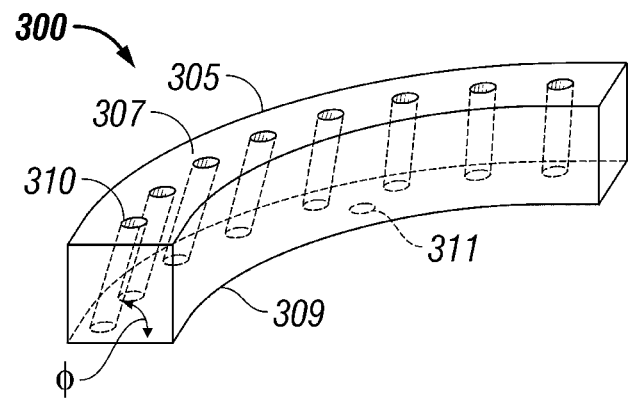
FIGS. 3A-3C are perspective schematic views of another embodiment of an ablation needle guide according to the present disclosure having angled needle slots.
Figure 3B:
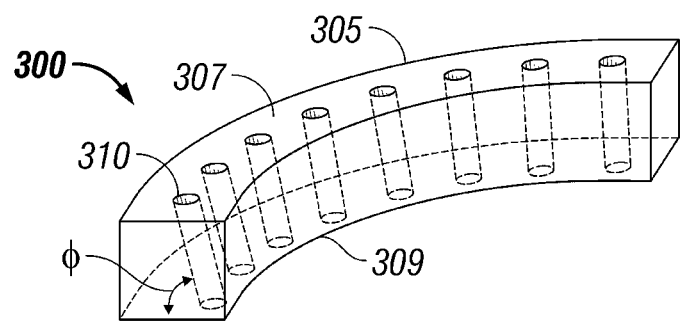
Figure 3C:
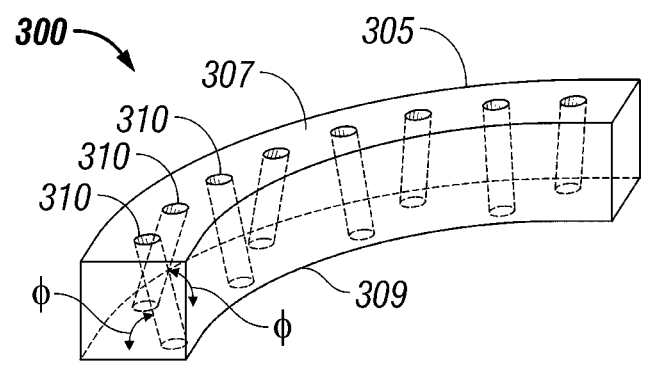

FIGS. 3A and 3B show another embodiment of a guide block 300 which includes an elongated, generally rectangular bar 305 which is selectively malleable or bendable to optimally position electrodes 1, 2 and/or 3 around a target site. The bar 305 includes a plurality of angled slots 310 disposed therethrough which are configured to selectively position and retain the electrodes 1, 2 and/or 3 at an angle relative to the target tissue. The slots 310 are disposed at an angle (φ) relative to top and bottom surfaces 307 and 309, respectively, of the bar 305. Disposing the electrodes at an angle relative to the target tissue "T" may enable the surgeon to create smaller and more precise ablation regions by radiating the heat at an angle towards the target tissue "T".

FIG. 3A shows the slots 310 angling away from the inner periphery and the bar 305 and FIG. 3B shows the slots 310 angling towards the inner periphery of the bar 305. The slots 310 may be disposed at alternating angles relative to the top and bottom surfaces 307 and 309, respectively. In one embodiment the bar 305 may be partially malleable and pre-disposed to have an inner periphery arched in a particular direction with the slots 310 directed toward or away from the inner peripheral arch (as shown in FIGS. 3B and 3A, respectively). However, it is also contemplated that the bar 305 may be fully malleable such that the angle of the slots 310 maybe oriented by bending the bar 305 in a given direction.

Figure 4A:
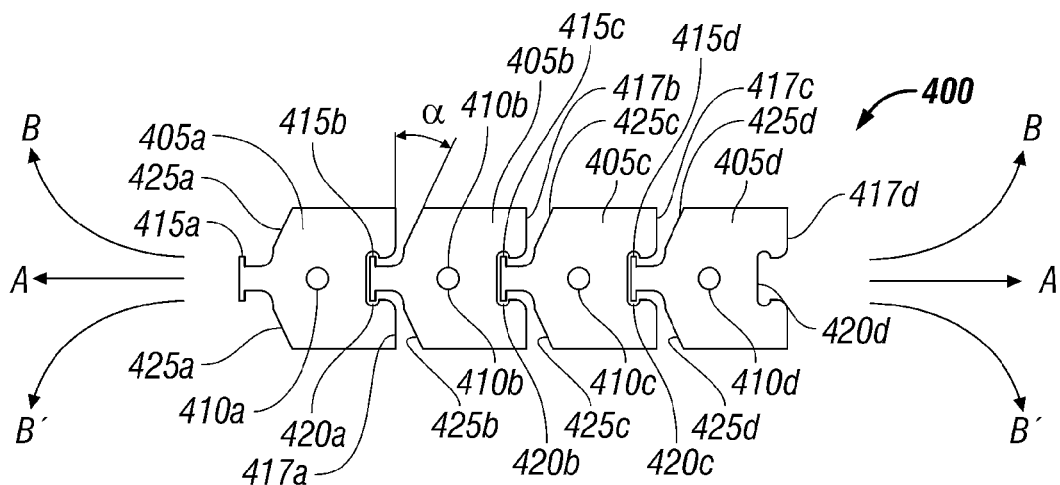
FIG. 4A is a schematic top view of another embodiment of a bendable ablation needle guide according to the present disclosure having a series of needle guide blocks arranged in a nested series with the needle holes centrally positioned within each ablation needle block.
Figure 4B:
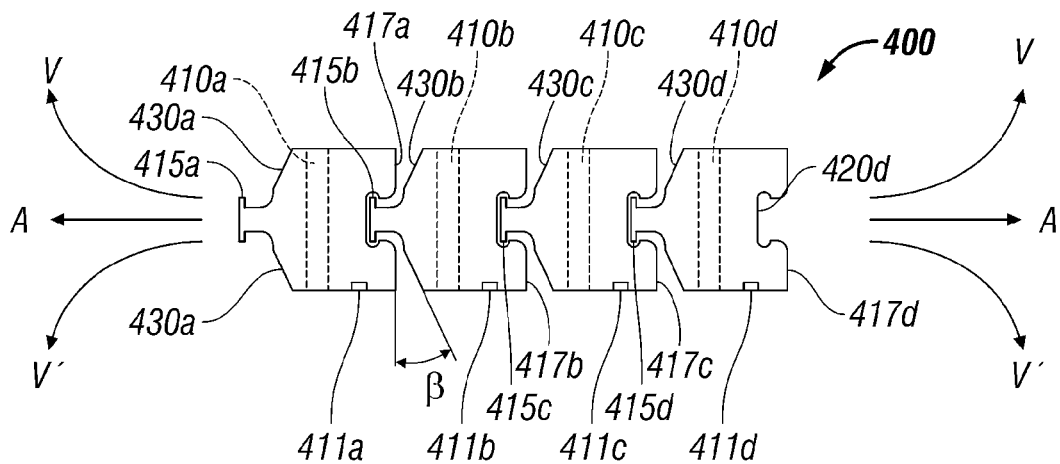
FIG. 4B is a schematic side view of the ablation needle block of FIG. 4A.

FIGS. 4A and 4B show top and side views of another embodiment of a guide block 400 which is segmented to facilitate orientation of the guide block 400 relative to a target tissue "T" to optimize electrode positioning. More particularly, guide block 400 includes a plurality of segments 405a-405d which nestingly engage one another to form guide block 400. Each individual segment is rotatable relative to a longitudinal axis A-A defined through the guide block 400. Any number of segments 405a-405x may be utilized to suit a particular surgical purpose or to arrange a particular electrode ablation around or relative to a target tissue "T". Each segment, e.g., segment 405a, is generally square-like and includes a male interface 415a and a female interface 420b which are configured to matingly engage corresponding male and female interfaces 415b-415d, 420b-420d, respectively of adjacent segments, e.g., 405b-405d such that the segments 405a-405d may be compiled or assembled to form guide block 400. Each segment 405a-405d also includes a slot 410a-410d disposed therethrough which is configured to selectively receive and retain an electrode 1, 2 and/or 3 therein for targeting tissue.

Each segment 405a-405d may also include a reference surface (or reference feature 411a-411d, respectively—See FIG. 4B) that is oriented in a specific fashion to create a reference surface image such that the ultrasonic scanner head 15 can mate therewith (or be easily oriented with respect thereto) to facilitate placement of the electrodes 1, 2 and 3. Reference features 411a-411d are configured to interact with the ultrasonic scanner head 15 and provide a point of reference to each respective segment 405a-405d to facilitate positioning of the electrodes 1, 2, and 3.

As best shown in FIG. 4A, each segment 405a-405d also includes opposing side facets 425a-425d, respectively, which are angled at a particular angle alpha (α) relative to a rear surface 417a-417d of a prior, adjacent segment 405a-405d when nested in series. The relative angle alpha (α) allows each segment 405a-405d to bend in a side direction in the direction of arrows "B" or "B'" relative to an adjacent segment 405a-405d (and relative to longitudinal axis A-A) to form a variety of block configurations around or relative to a target tissue "T".

FIG. 4B shows a side view of the guide block 400 which includes the same elements as described above with respect to FIG. 4A with the exception that each segment, e.g., segment 405a, includes opposing top and bottom facets, e.g., facets 430a. The facets 430a-430b on segments 405a-405b are angled at an angle beta (β) relative to the rear surface 417a-417b of a prior, adjacent segment 405a-405b when nested in series. This allows the guide block to flex in a vertical direction "V" or "V'" relative to an adjacent segment 405a-405b to match the various anatomical contours surrounding a particular target tissue "T" site.

As can be appreciated, the guide block 400 may be arranged with any number of segments 405a-405x which facilitate positioning electrodes around or relative to a target tissue "T" site. For example, the guide bar 400 may be bent to form a circle, partial circle (arc), serpentined (or "S" shaped) or straight depending upon a particular surgical condition. Moreover, the guide bar 400 may be flexed in a vertical direction to match anatomical profiles.

Figure 5A:
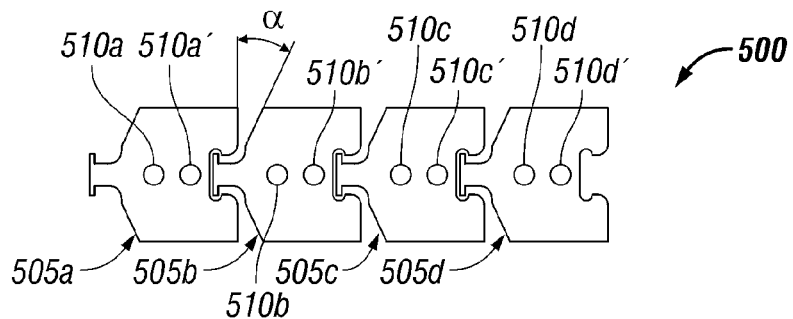
FIG. 5A is a schematic top view of another embodiment of a bendable ablation needle guide according to the present disclosure having a series of needle guide blocks arranged in a nested series with the two needle holes positioned within each ablation needle block.
Figure 5B:
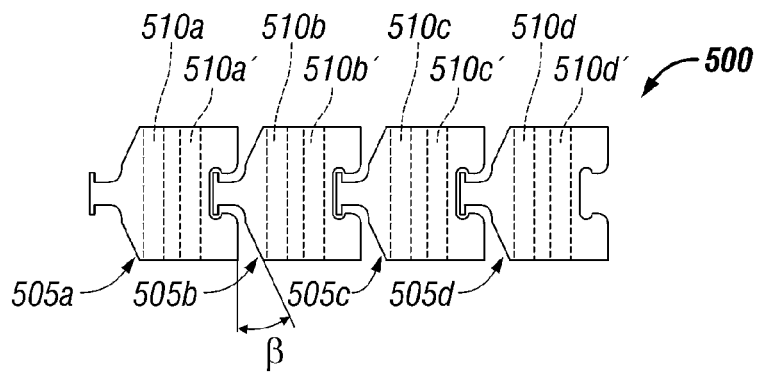
FIG. 5B is a schematic side view of the ablation needle block of FIG. 5A.

FIGS. 5A and 5B show another embodiment of a guide block 500 very similar to the guide block of FIGS. 4A and 4B with the exception that a pair of needle slots, e.g., needle slots 510a and 510a' are positioned through each segment, e.g., segment 505a. Each pair, e.g., pair 510a and 510a', 510b and 510b', 510c and 510c' and 510d and 510d' allow more electrodes 1, 2 and/or 3 to be positioned or repositioned within each segment 505a, 505b, 505c and 505d of guide block 500 thereby creating a different line, shape, plane or plume of treated tissue.

Figure 6A:
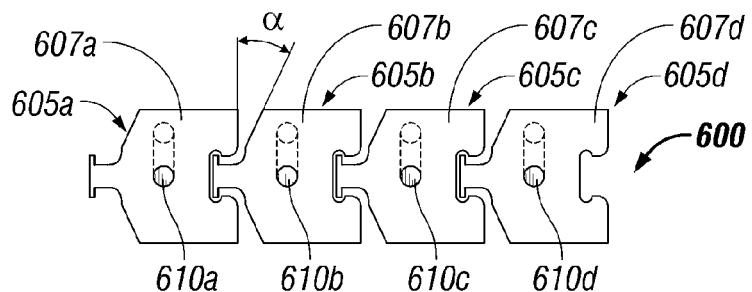
FIG. 6A is a schematic top view of another embodiment of a bendable ablation needle guide according to the present disclosure having a series of needle guide blocks arranged in a nested series with the needle hole being angled through each ablation needle block.
Figure 6B:
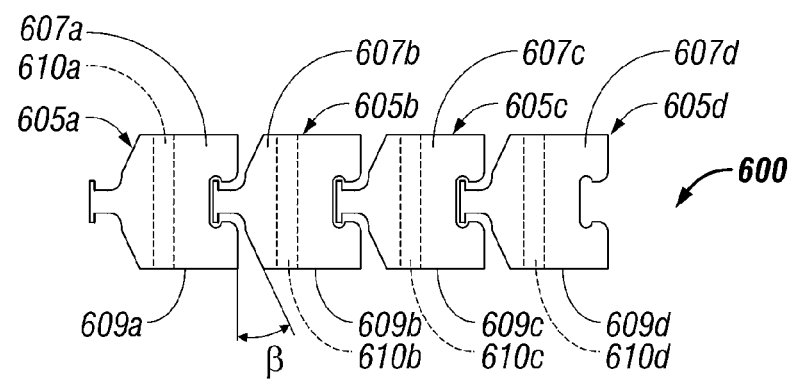
FIG. 6B is a schematic side view of the ablation needle block of FIG. 6A.

FIGS. 6A and 6B show yet another embodiment of a guide block 600 again very similar to the guide block of FIGS. 4A and 4B with the exception that one or more of the needle slots, e.g., needle slots 610a-610d, are angled relative to the top 607a-607d and bottom surfaces 609a-609d through each respective segment 605a-605d. Each respective needle slot, e.g., needle slot 610a, of each respective segment 605a may be angled differently from an adjacent slot, e.g., 610b of another segment 605b. In another embodiment and as shown in FIGS. 7A and 7B, the guide bock 700 may include multiple segments 705a-705d with slots 710a-710d and slot 710a'-710d' wherein each, e.g., slot 710a, is be angled through the guide block 700 at one angle (e.g., towards one side of the guide block 700 as the slot 710a transverses from the top surface 707 to the bottom surface 709) and a second slot in each segment, e.g., 710a', is angled through the guide block 700 in a mirrored fashion to slot 710a thereby creating a different line, shape, plane or plume of treated tissue.

Figure 7A:
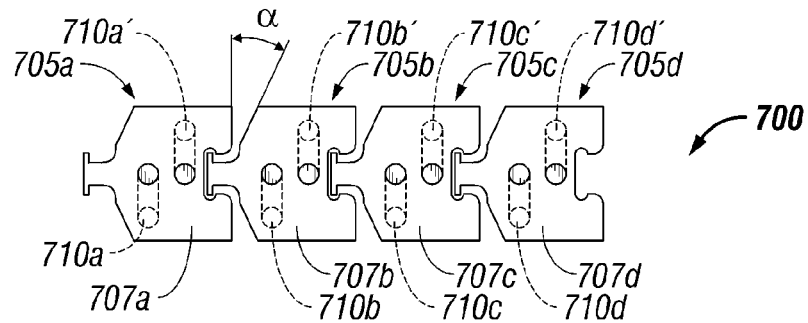
FIG. 7A is a schematic top view of another embodiment of a bendable ablation needle guide according to the present disclosure having a series of needle guide blocks arranged in a nested series with two needle holes in each block, each needle hole of each block being angled through each ablation needle block at different a angle from the corresponding needle hole of each ablation needle block.
Figure 7B:
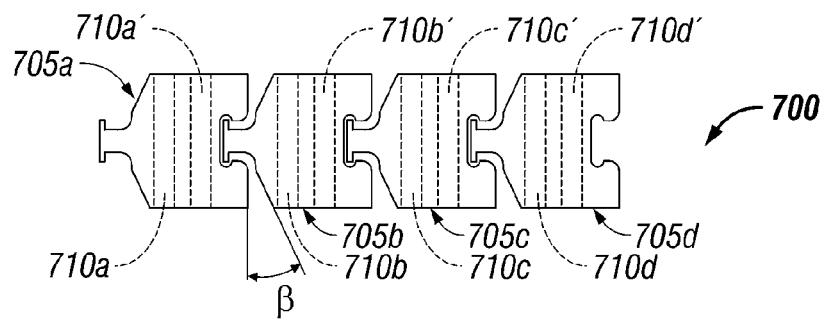
FIG. 7B is a schematic side view of the ablation needle block of FIG. 7A.
Figure 8A:
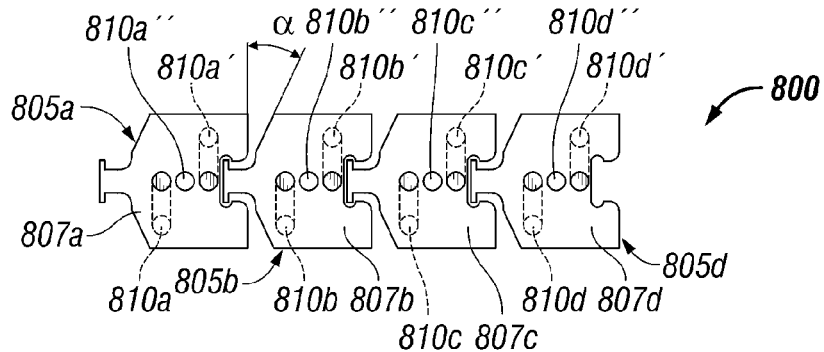
FIG. 8A is a schematic top view of another embodiment of a bendable ablation needle guide similar to the embodiment of FIG. 7A with each ablation needle block including a centrally disposed needle hole in each block along with the angled needle holes.
Figure 8B:
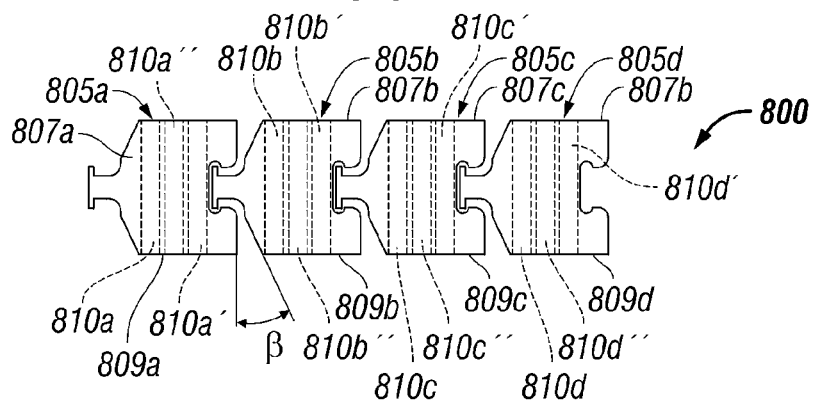
FIG. 8B is a schematic side view of the ablation needle block of FIG. 8A.

FIGS. 8A and 8B show another embodiment according to the present disclosure similar to FIGS. 7A and 7B wherein each segment 805a-805d of the guide block 800 includes three slots 810a-810d, 810a'-810d' and 810a"-810d", respectively, disposed therethrough for supporting, retaining and/or repositioning three corresponding electrodes 1, 2 and/or 3 (See FIG. 1). Slots 810a-810d are disposed at a first angle relative to the top 807a-807d and bottom 809a-809d surfaces through each segment 805a-805d, respectively, slots 810a'-810d' are disposed at a second angle relative to the top 807a-807d and bottom 809a-809d surfaces through each segment 805a-805d, respectively, and slots 810a"-810d" are disposed at a third angle relative to the top 807a-807d and bottom 809a-809d surfaces through each segment 805a-805d, respectively. One or more of the slots 810a-810d may be disposed at a normal orientation relative to the top 807a-807d and bottom 809a-809d surfaces.

Figure 9A:
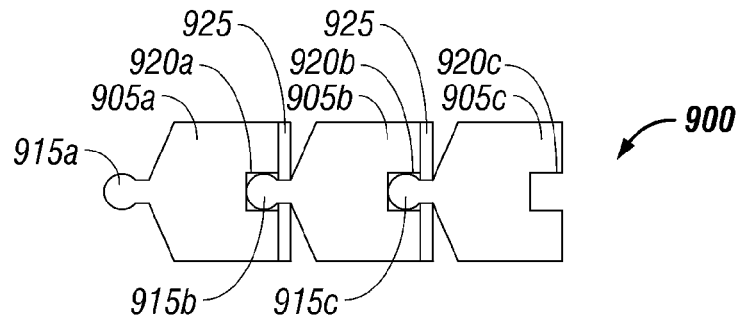
FIG. 9A is a schematic top view of another embodiment of an ablation needle block according to the present disclosure including a locking clip for retaining each ablation needle block nested to an adjacent ablation needle block.
Figure 9B:
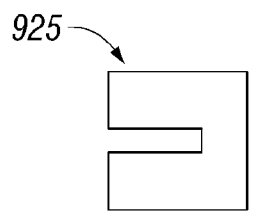
FIG. 9B is a front view of the locking clip of the ablation needle block of FIG. 9A.

FIGS. 9A and 9B show another embodiment of a guide block 900 according to the present disclosure similar to the nested embodiments of FIGS. 4A-8B wherein a locking clip 925 is utilized to provide mechanical engagement of two adjacent segments, e.g., segments 905a and 905b. More particularly, each segment, e.g., 905a, is dimensioned to include a first mechanical interface, e.g., a male interface 915a, and a second mechanical interface, e.g., a female interface 920a. The second or female interface 920a of a segment 905a is designed to mechanically receive the male interface 915b of segment 905b. The locking clip 925 is configured as a generally C-shaped clip which is dimensioned to engage and lock the male interface 915b within the female interface 920a of two adjacent segments 905a and 905b. Each nested and adjacent pair would include a locking clip 925 to securely engage the two segments in nested series.

Figure 10A:
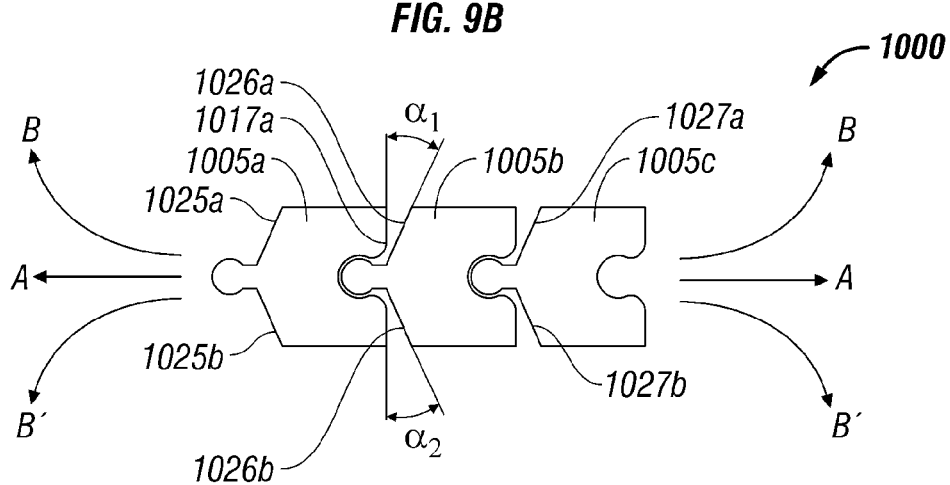
FIG. 10A is a schematic top view of another embodiment of an ablation needle block according to the present disclosure showing a series of nested ablation needle blocks each having an inner face with a first bend angle and an outer face with a second bend angle for bending the ablation needle guide at different angles in a transverse plane.
Figure 10B:
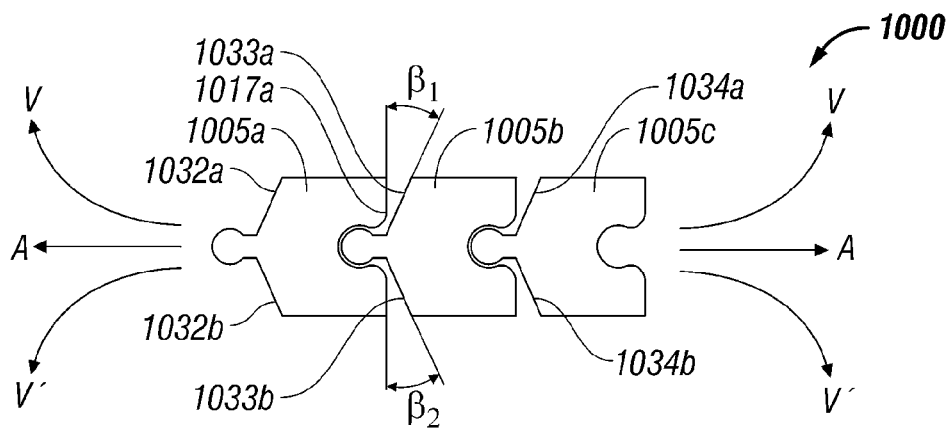
FIG. 10B is a schematic side view of the embodiment of FIG. 10A showing the top and bottom faces having different bend angles for bending the ablation needle guide at different angles in a vertical plane.

FIGS. 10A and 10B show yet another embodiment of a guide block 1000 according to the present disclosure which includes a nested arrangement of segments 1005a-1005c having interlocking mechanical interfaces. More particularly, each segment, e.g., segment 1005b, includes a first angled side face of facet 1026a having a first angle α1 relative to the rear surface 1017a of a distally adjacent segment 1005a and a second angled side face of facet 1026b having a second angle α2 relative to the rear surface 1017a of a distally adjacent segment 1005a. This arrangement of angles allows the guide block 1000 a particular range of movement in a transverse direction depending upon the bend direction "B" or "B'" of the guide block 1000. FIG. 10B shows a similar arrangement wherein the top and bottom facets 1033a and 1033b, respectively, of segment 1005b include different angles β1 and β2 relative to the rear surface 1017a of segment 1005a. This arrangement of angles allows the guide block 1000 a particular range of movement in a vertical direction depending upon the bend direction "V" or "V'" of the guide block 1000.

Figure 11A:
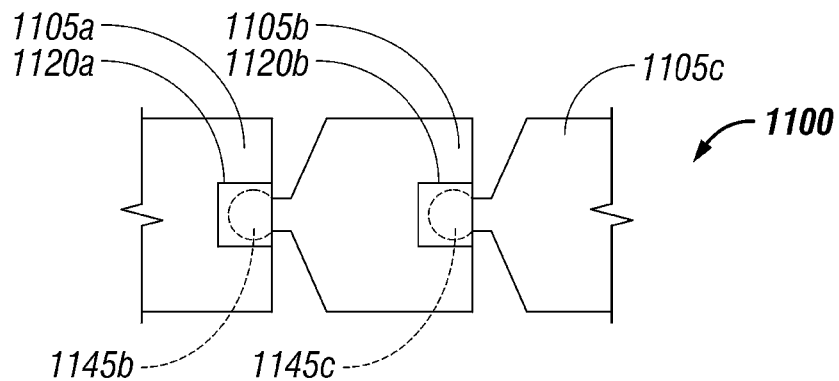
FIG. 11A is a schematic bottom view of another embodiment of an ablation needle block.
Figure 11B:
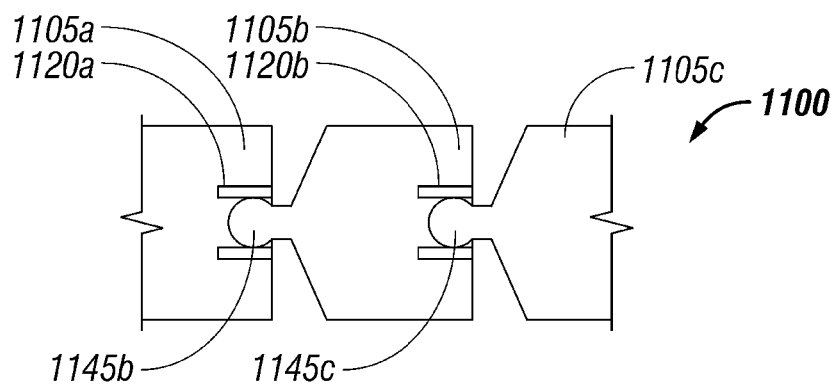
FIG. 11B is a schematic top view of the ablation needle block of FIG. 11A.
Figure 11C:
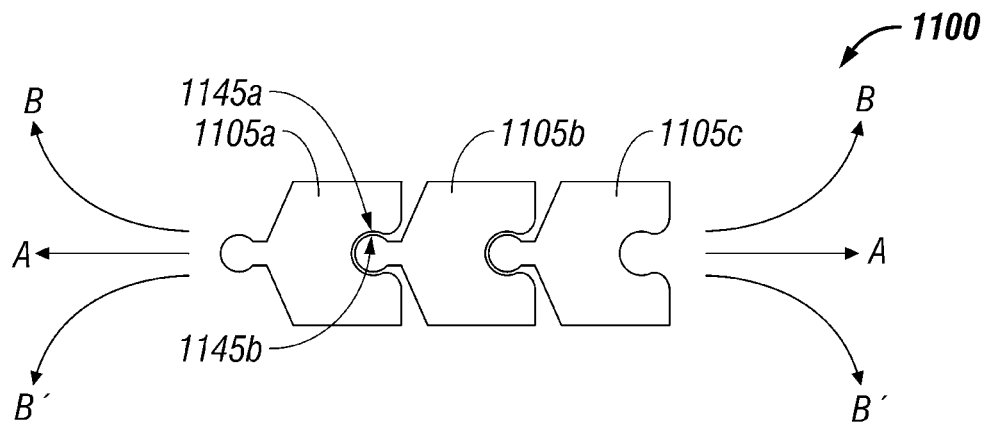
FIG. 11C is a schematic top view of another embodiment of an ablation needle block.
Figure 11D:
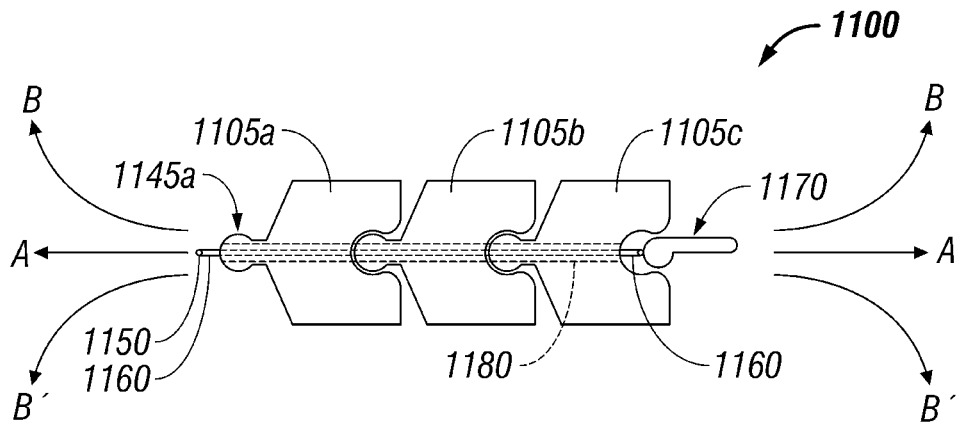
FIG. 11D is a schematic top view of another embodiment of an ablation needle block including a locking system illustrated in a first orientation.
Figure 11E:
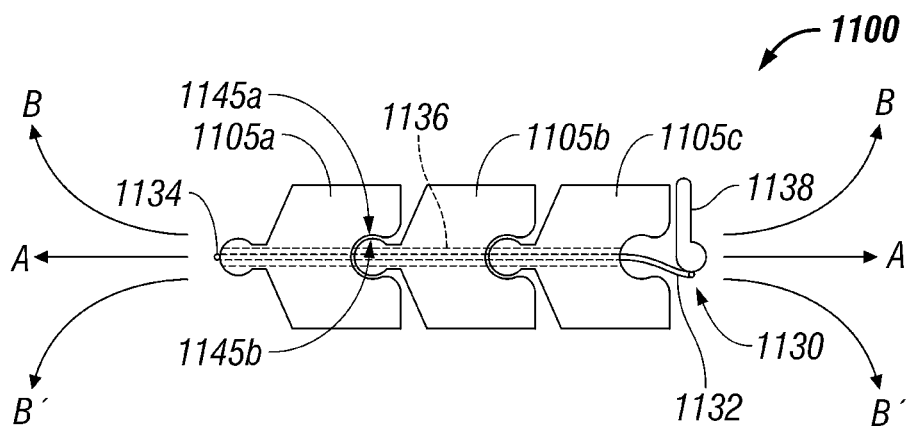
FIG. 11E is a schematic top view of the ablation needle block of FIG. 11D illustrating the locking system in a second orientation.

FIGS. 11A and 11B show still another embodiment of a guide block 1100 according to the present disclosure which includes a friction-fit mechanical interface between nested segments 1105a-1105c. More particularly, each segment, e.g., segment 1105a, includes female interface 1120a which is dimensioned to frictionally engage a corresponding male interface 1145b of a proximally adjacent segment 1105b. The friction-fit may be two-dimensional in nature, i.e., the mechanical interfaces 1145b and 1120a are frictionally engaged on two opposing sides like a cuff-like arrangement, e.g., as shown in FIG. 11B, or three dimensional wherein the two mechanical interfaces 1145b and 1120a are frictionally engaged on all sides like a friction-fit ball and socket arrangement (See FIG. 11C). The other male and female mechanical interfaces, namely, interfaces 1145c and 1120b, may be configured to engage in a similar fashion or in a different manner (e.g., as described above) depending upon a particular purpose.

FIGS. 11D-11G show yet another embodiment of a guide block that includes a friction-fit locking system 1130 which is operable to lock the guide block 1100 in a given orientation to facilitate positioning and placement of electrode 1, 2 and 3. More particularly, friction-fit locking system 1130 includes a toggle-like lever 1138 that is secured at a remote end 1134 by a cable 1132 disposed through a channel 1136 define in the guide block 1100. The lever 1138 is operable from a first orientation (See FIG. 11D) which allows free positioning and angling of the nested guide segments 1105a-1105c as explained above to a second orientation (See FIG. 11E) that tensions the cable 1132 and secures the nested segments 1105a-1105c relative to one another at a desired angled orientation.

Figure 11F:
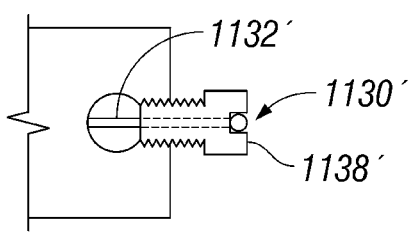
FIG. 11F is a top view of an embodiment of a tensioning system of a guide block illustrating the tensioning system in a first orientation.
Figure 11G:
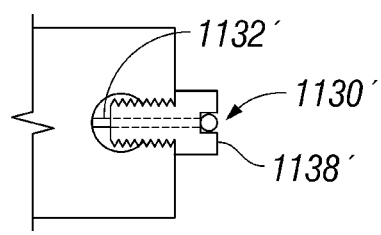
FIG. 11G is a top view of the tensioning system of FIG. 11F illustrated in a second orientation.

FIGS. 11F-11G show an alternate tensioning system 1130' which utilizes a screw member 1138' to secure the segments 1105a-1105c relative to one another in a desired orientation. More particularly, the screw member 1138' is rotatable from a first orientation (See FIG. 11G) which allows the segments 1105a-1105c to be freely manipulatable relative to one another to orient the guide block 1100 for positioning of the electrodes 1, 2, and 3 to a subsequent position (Shown in FIG. 11F) which tensions the cable 1132' to lock the nested segments 1105a-1105c relative to one another at a desired angled orientation.

Figure 12:
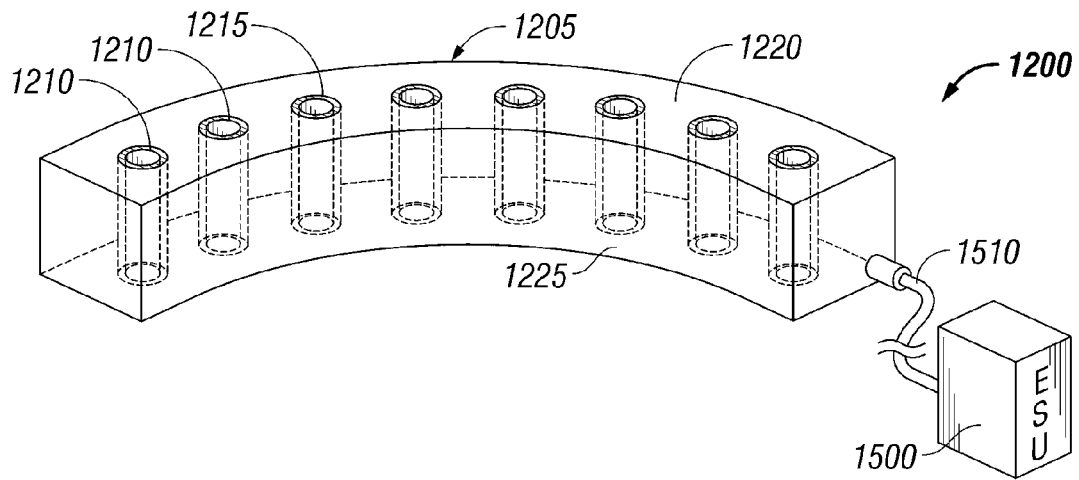
FIG. 12 is a schematic perspective view of another embodiment of an ablation needle block according to the present disclosure wherein the needle guide block acts as an electrical return path and the needle holes are insulated therefrom by a dielectric material.

FIG. 12 shows yet another embodiment of a guide block 1200 according to the present disclosure which includes a generally rectilinear, elongated bar 1205 having a series of slots 1210 disposed therethrough configured to selectively receive and retain a corresponding series of electrodes 1, 2 and/3 (See FIG. 1) therein for ablating tissue. More particularly, the rectilinear bar 1205 includes top and bottom surfaces 1220 and 1225, respectively, which include the series of slots 1210 disposed therebetween that support the electrodes 1, 2 and/or 3 for sequential or simultaneous activation depending upon a particular surgical purpose. The bar 1205 in this instance may be malleable (or bendable) along one or more planes or may be rigid and include a pre-formed configuration from substantially straight to substantially curved.

The bar 1205 is configured to act as a return electrode and includes at least one portion, e.g., bottom surface 1225, which is electrically conductive and engages a tissue surface. During activation, the bottom surface carries the return potential back to an electrosurgical generator 1500 via cable 1510. Each slot 1210 includes a dielectric material 1215 disposed along the inner periphery thereof which isolates the electrodes 1, 2 and 3 and the remaining portions of bar 1205 from the bottom surface 1225 (or other conductive portions) during activation.

Figure 13:
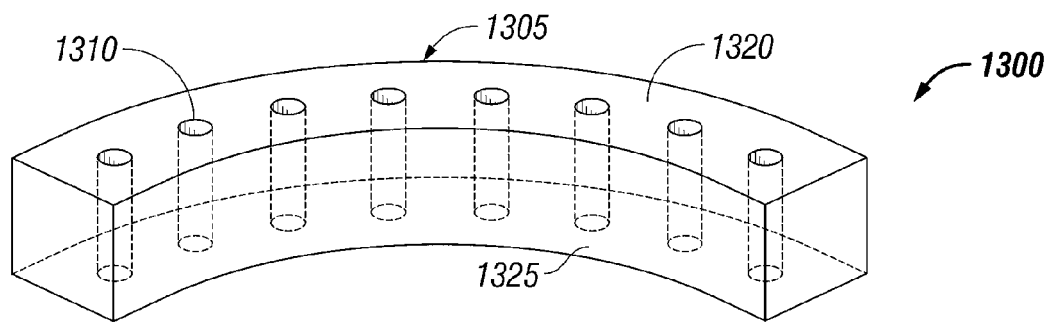
FIG. 13 is a schematic illustration of another embodiment of an ablation needle guide for guiding heated ablation needles to a targeted tissue area including a thermally conductive bottom surface to absorb heat during the ablation procedure.
Figure 14:
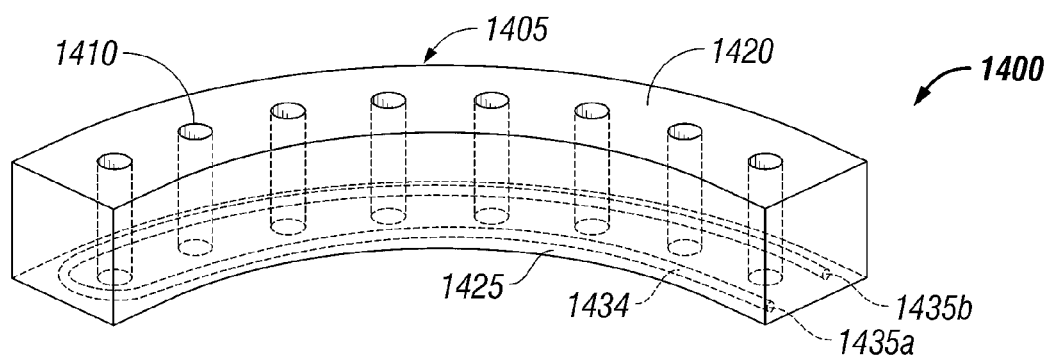
FIG. 14 is a schematic illustration of another embodiment of an ablation needle guide for guiding heated ablation needles to a targeted tissue area including a cooling loop disposed therein for absorbing heat during the ablation procedure.
Figure 15:
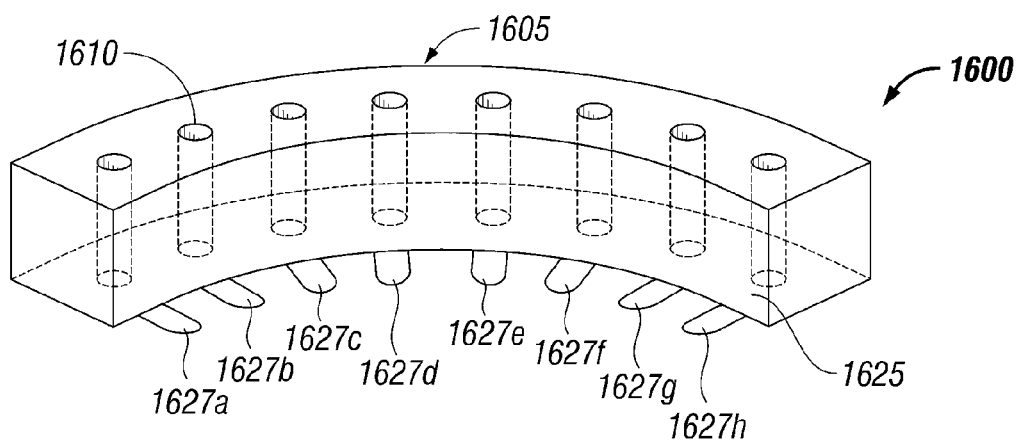
FIG. 15 is a schematic illustration of another embodiment of an ablation needle guide including a plurality of fins which extend outwardly from the bottom surface to absorb heat during the ablation procedure.
Figure 16:
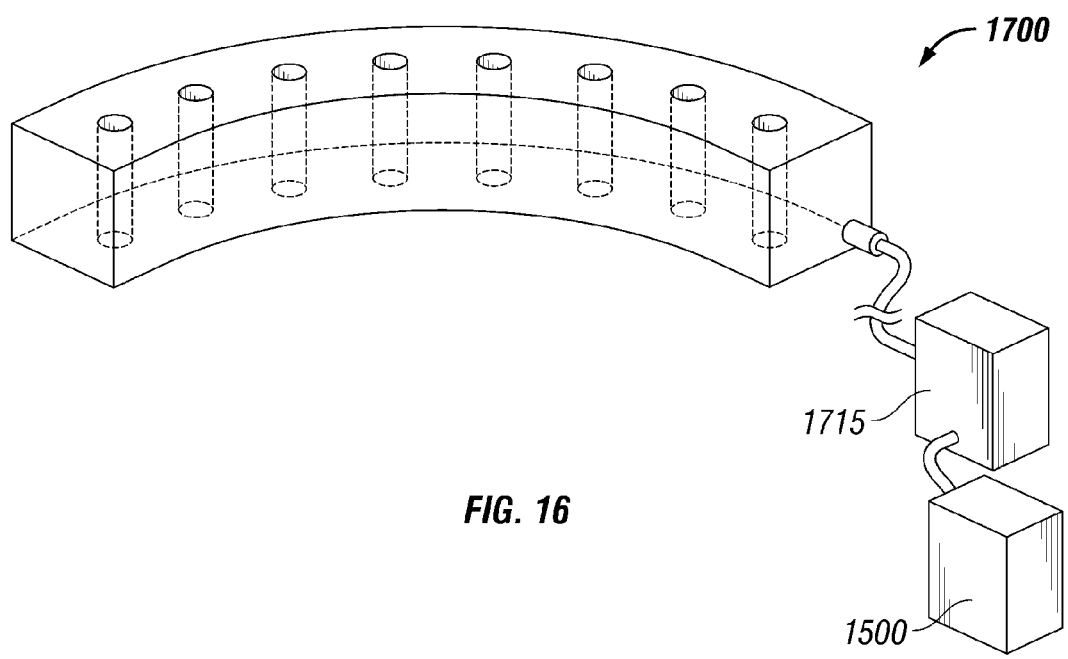
FIG. 16 is a schematic illustration of another embodiment of an ablation needle guide having an audio feedback sensor for providing feedback to the generator relating to the status of the ablation procedure.

In one embodiment and as shown in FIG. 13, the bottom surface 1325 of guide block 1300 may be configured to act as a heat sink to dissipate heat during activation of the electrodes 1, 2 and/or 3 (See FIG. 1). In this instance a portion of the bar 1305, e.g., bottom surface 1325, may be made from a thermally conductive and electrically non-conductive material. The thermally conductive bottom surface 1325 is designed to effectively absorb or thermally dissipate the heat during electrosurgical activation and generally restrict heat travel beyond intended target tissue areas. In other words, the material acts like a "heat sink" to limit thermal damage to surrounding tissue. The thermally conductive bottom surface 1325 is also electrically non-conductive which also restricts current concentrations to intended tissue areas.

The thermally conductive bottom surface 1325 may be made from a material having a high thermal conductivity value or "k" value and minimum electrical conductively, e.g., anodized aluminum. Alternatively, the thermally conductive surface 1325 may be made from or combined with a semi-resilient or elastomeric material to correspond to the malleability of the bar 1305 and top surface 1320. Examples of thermally conductive and electrically non-conductive materials which can be utilized to minimize thermal damage to surrounding tissue include, but are not limited to: thermally conductive plastic materials which dissipate heat along a preferred isothermal profile to the surrounding environment resulting in a lower maximum temperature and reduced formation of hot spots. Examples of such materials are commonly sold under the trademark CoolPoly® by Cool Polymers, Inc., of Rhode Island and composite materials such as $ALO_2$.

In yet another embodiment, a thermally conductive system may be used with a guide block 1400 and act as an active cooling system that surrounds a portion, e.g., bottom surface 1425, of bar 1405 to reduce heat dissipation to surrounding tissue. More particularly, a series of ducts or tubes 1434 (shown in phantom) may be disposed through bar 1405 proximate the bottom tissue engaging surface 1425 which supply active cooling liquid (preferably, non-electrically conductive cooling liquid) or gas (e.g., air) to a series of nozzles or ports 1435a and 1435b located adjacent the bottom surface 1425 of the bar 1405. The system supplies coolant (liquid or gas (e.g., air)) to the tissue areas adjacent the ablation site to actively cool the tissue during activation which reduces thermal spread.

In yet another embodiment according to the present disclosure, the guide block 1600 includes a rectilinear guide bar 1605 having a bottom surface 1625 which engages tissue and a series of fin-like extensions 1627a-1627f which extend laterally from each side therefrom which are configured to absorb or dissipate heat emanating from the ablation site. The fins 1627a-1627f may be shaped and dimensioned to facilitate manufacturing, assembly and manipulability relative to the target tissue site. Ideally, two fins, e.g., fins 1627a and 1627b, are disposed on either side of an electrode slot to maximize heat dissipation during activation. The fins 1627a-1627f may also enhance stability of the guide block 1600 during a given surgical procedure.

In still another embodiment according to the present disclosure, the guide block 1700 may be configured to connect to a smart type generator 1500 which includes additional features designed to enhance or facilitate the ablation process. For example, the generator 1500 may include an audio feedback sensor 1715 (or the like) which provides real time feedback to the generator 1500 relating to the ablation progress and may provide auditory or visual signals to the surgeon relating to an "ABLATE ON", "ABLATE OFF" or "OKAY TO REPOSITION" status relating to one or more of the electrodes 1, 2 and/or 3. The generator 1500 may also include an algorithm which provides the user with a timer countdown for re-activation of one or more electrodes 1, 2 and/or 3 after an "OFF" period. The timer countdown algorithm may be selectively programmable, automatic or manual and may be activated upon repositioning of one or more electrodes 1, 2 and/or 3.

Moreover the generator 1500 may include an adaptive baseline algorithm which automatically resets the impedance baseline relative to an impedance threshold or "time out" value or condition after each ablation cycle. Still further, the generator 1500 may include a variable tone or visual signal algorithm which tracks the impedance in the tissue as the impedance changes from low to high to completed cycle.

The present disclosure also relates to a method for positioning a guide block, e.g., guide blocks 200-1400,1600 and 1700, relative to a target site for ablation, the method includes the initial step of providing a guide block, e.g., guide blocks 200-1400,1600 and 1700, including a series of slots defined therethrough for selectively receiving and positioning electrodes therein. The method also includes the steps of: placing at least one electrode, e.g., electrode 1, into one of the needle slots in the guide block e.g., slot 210 and guide block 200; using an image scanner 30 to orient the angle of the electrode 1 relative to the target tissue; manipulating the guide block 200 transversally and/or vertically to orient the guide block 200 relative to the target tissue and preferred resection plane; inserting additional electrodes 2 and 3 into the guide block 200 along preferred resection line; activating one or more electrodes 1,2 and/or 3 either sequentially or simultaneously to ablate tissue; resecting tissue along the resection line. Alternatively, one or more electrodes 1, 2 and/or 3 may be repositioned into remaining slots 210 after each ablation cycle to form the resecting line.

From the foregoing and with reference to the various figure drawings, those skilled in the art will appreciate that certain modifications can also be made to the present disclosure without departing from the scope of the same. For example, it should be understood that variations in the choice of electrical output parameters from the electrosurgical generator, to control or monitor the electrode array ablation process, may vary widely depending on the operator's experience, technique, or preference. For example, in the embodiments above, a common RF voltage is applied to all of the electrodes of the array simultaneously. As an alternate embodiment, in accordance with the present disclosure, the clinician may choose to control the RF current to the individual electrodes of the array or the total current of the array as a whole. Voltage variations on each electrode could be applied to achieve constant current output from each electrode. Alternatively, constant power output from each electrode may be sought in some clinical settings. Voltage variations or phases between electrodes may be implemented to achieve desired temperature distribution in the tissue as monitored by temperature sensors in the tissue or by visualization of temperature distribution using thermally sensitive MRI scanning, for example. Accordingly, the choice of electrical output type, sequence, and levels and the distribution of the electrodes of the array should be considered to have wide variations within the scope of the present disclosure. Moreover, the various guides contemplated herein may be configured and sized for implementation with various types of electrosurgical devices such as microwave, ultrasonic, cryopreservation, radiofrequency, etc.

While various embodiments of the disclosure have been described, it is not intended that the disclosure be limited thereto, as it is intended that the disclosure be as broad in scope as the art will allow and that the specification be read likewise. Therefore, the above descriptions should not be construed as limiting, but merely as exemplifications of preferred embodiments. Those skilled in the art will envision other modifications within the scope and spirit of the claims appended hereto.

What is claimed is:

1. A guide block for introducing electrodes into target tissue, comprising:
   an elongated bar having a top surface and a bottom surface configured to contact tissue, the elongated bar defining a plurality of slots that extend through the top and bottom surfaces, each slot of the plurality of slots configured to receive an electrode therethrough, the plurality of slots including a first plurality of slots disposed at a first angle relative to the top and bottom surfaces and a second plurality of slots disposed at a second angle relative to the top and bottom surfaces, the first and second plurality of slots angled away from each other with respect to both the top and bottom surfaces of the elongated bar and disposed at alternating angles relative to the top and bottom surfaces of the elongated bar; and
   an electrically conductive portion forming a portion of the bottom surface of the elongated bar.

2. The guide block according to claim 1, further comprising a cable including:
   a first end coupled to the elongated bar and configured to electrically connect to the electrically conductive portion; and
   a second end configured to couple to a generator such that the electrically conductive portion returns electrical energy back to the generator.

3. The guide block according to claim 1, wherein the elongated bar includes a dielectric material disposed in at least one slot of the plurality of slots.

4. The guide block according to claim 3, wherein the dielectric material lines an inner periphery of the at least one slot of the plurality of slots.

5. The guide block according to claim 4, wherein the dielectric material has a cylindrical configuration.

6. The guide block according to claim 1, wherein the elongated bar has a rectilinear shape.

7. The guide block according to claim 1, wherein the elongated bar is malleable and selectively bendable between a linear configuration and a curved configuration.

8. The guide block according to claim 1, wherein each slot of the plurality of slots has a top opening that is coplanar with the top surface and a bottom opening that is coplanar with the bottom surface.

* * * * *